United States Patent [19]
Schubert et al.

[11] Patent Number: 5,932,415
[45] Date of Patent: Aug. 3, 1999

[54] PROCESSES AND AGENTS FOR DETECTING LISTERIAS

[75] Inventors: Peter Schubert, Darmstadt; Siegfried Neumann, Seeheim-Jugenheim; Martina Pawelzik, München; Winfried Linxweiler, Gross-Umstadt; Christa Burger, Darmstadt; Gottfried Hofmann, Darmstadt; Andreas Bubert, Gerbrunn; Werner Goebel, Veitshöchheim, all of Germany; Stefan Köhler, St. Clément de Revière, France

[73] Assignee: Merck Patent Gesellschaft Mit, Beschrankter Haftung, Germany

[21] Appl. No.: 08/456,670

[22] Filed: Jun. 1, 1995

Related U.S. Application Data

[62] Division of application No. 08/412,227, Mar. 27, 1995, abandoned, which is a continuation of application No. 08/075,248, Jun. 11, 1993, abandoned.

[30] Foreign Application Priority Data

Jun. 11, 1992 [DE] Germany ................. 4219111
Nov. 26, 1992 [DE] Germany ................. 4239567

[51] Int. Cl.$^6$ ............... C12Q 1/68; C12P 19/34; G01N 33/53; C07H 21/04
[52] U.S. Cl. ............... 435/6; 435/91.2; 435/975; 536/23.7
[58] Field of Search ............... 536/23.7; 435/6, 435/91.2, 975

[56] References Cited

PUBLICATIONS

Köhler, et al., Infection and Immunity, vol. 58, No. 6, pp. 1943–1950 (Jun. 1990).

Datta, et al., Applied and Environmental Microbiology, vol. 54, No. 12, pp. 2933–2937 (Dec. 1988).

Deneer, et al., Applied and Environmental Microbiology, vol. 57, No. 2, pp. 606–609 (Feb. 1991).

Border, et al., Letters in Applied Microbiology, vol. 11, pp. 158–162 (1990).

Furrer, et al., Journal of Applied Bacteriology, vol. 70, pp. 373–379 (1991).

Lerner, Adv in Immunol., vol. 36, pp. 1–44 (1984).

*Primary Examiner*—Anthony C. Caputa
*Assistant Examiner*—Mark Navarro
*Attorney, Agent, or Firm*—Millen, White, Zelano, & Branigan, P.C.

[57] ABSTRACT

The invention relates to agents and processes for detecting bacteria of the genus Listeria, in particular *L. monocytogenes*. The agents according to the invention include primers whose sequence is selected from the iap gene of *L. monocytogenes*. In addition, the agents according to the invention include peptides whose sequence is selected from the p60 protein and which are suitable for producing specific antibodies for the immunological detection of *L. monocytogenes*.

6 Claims, 7 Drawing Sheets

Val Ser Thr Pro Val Ala Pro Thr Gln
1                    5

FIG. 2a

Thr Thr Gln Ala Thr Thr Pro Ala Pro Lys Val Ala
1                    5                   10

FIG. 2b

Leu Ala Ile Lys Gln Thr Ala Asn Thr Ala Thr
1                    5                   10

FIG. 2c

Gln Gln Gln Thr Ala Pro Lys Ala Pro Thr Glu
1                    5                   10

FIG. 2d

Ser Thr Pro Val Ala Pro Thr Gln Glu Val Lys Lys
1                    5                   10

FIG. 2e

Pro Val Ala Pro Thr Gln Glu Val Lys Lys
1                    5                   10

FIG. 2f

Gln Val Asn Asn Glu Val Ala Ala Ala Glu Lys Thr Glu Lys
1                    5                           10

FIG. 2g

Glu Val Lys Gln Thr Thr Gln Ala Thr Thr Pro Ala
1                    5                   10

FIG. 2h

Ala Ile Lys Gln Thr Ala Asn Thr Ala Thr Pro Lys
1                    5                   10

FIG. 2i

```
Gln Val Asn Asn Glu Val Ala Ala Glu Lys Thr Glu Lys Ser Val
 1            5                   10                15

Ser Ala Thr Trp Leu Asn Val Arg Thr Gly Ala Gly Val Asp Asn Ser
             20                  25                  30

Ile Ile Thr Ser Ile Lys Gly Gly Thr Lys Val Thr Val Glu Thr Thr
             35              40                  45

Glu Ser Asn Gly Trp His Lys Ile Thr Tyr Asn Asp Gly Lys Thr Gly
     50              55                  60

Phe Val Asn Gly Lys Tyr Leu Thr Asp Lys Ala Val Ser Thr Pro Val
 65              70              75                          80

Ala Pro Thr Gln Glu Val Lys Lys Glu Thr Thr Thr Gln Gln Ala Ala
             85                  90                  95

Pro Val Ala Glu Thr Lys Thr Glu Val Lys Gln Thr Thr Gln Ala Thr
            100             105             110

Thr Pro Ala Pro Lys Val Ala Glu Thr Lys Glu Thr Pro Val Ile Asp
            115             120             125

Gln Asn Ala Thr Thr His Ala Val Lys Ser Gly Asp Thr Ile Trp Ala
        130             135             140

Leu Ser Val Lys Tyr Gly Val Ser Val Gln Asp Ile Met Ser Trp Asn
145             150              155             160

Asn Leu Ser Ser Ser Ser Ile Tyr Val Gly Gln Lys Leu Ala Ile Lys
                165             170             175

Gln Thr Ala Asn Thr Ala Thr Pro Lys Ala Glu Val Lys Thr Glu Ala
            180             185             190

Pro Ala Ala Glu Lys Gln Ala Ala Pro Val Val Lys Glu Asn Thr Asn
        195             200             205

Thr Asn Thr Ala Thr Thr Glu Lys Lys Glu Thr Ala Thr Gln Gln Gln
    210             215             220

Thr Ala Pro Lys Ala Pro Thr Glu
225             230
```

FIG. 3

Met Asn Met Lys Lys Ala Thr Ile Ala Ala Thr Ala Gly Ile Ala Val
1           5               10              15

Thr Ala Phe Ala Ala Pro Thr Ile Ala Ser Ala Ser Thr Val Val Val
            20              25              30

Glu Ala Gly Asp Thr Leu Trp Gly Ile Ala Gln Ser Lys Gly Thr Thr
            35              40              45

Val Asp Ala Ile Lys Lys Ala Asn Asn Leu Thr Thr Asp Lys Ile Val
    50              55              60

Pro Gly Gln Lys Leu Gln Val Asn Asn Glu Val Ala Ala Ala Glu Lys
65              70              75              80

Thr Glu Lys Ser Val Ser Ala Thr Trp Leu Asn Val Arg Thr Gly Ala
                85              90              95

Gly Val Asp Asn Ser Ile Ile Thr Ser Ile Lys Gly Gly Thr Lys Val
            100             105             110

Thr Val Glu Thr Thr Glu Ser Asn Gly Trp His Lys Ile Thr Tyr Asn
        115             120             125

Asp Gly Lys Thr Gly Phe Val Asn Gly Lys Tyr Leu Thr Asp Lys Ala
    130             135             140

Val Ser Thr Pro Val Ala Pro Thr Gln Glu Val Lys Lys Glu Thr Thr
145             150             155             160

Thr Gln Gln Ala Ala Pro Val Ala Glu Thr Lys Thr Glu Val Lys Gln
            165             170             175

Thr Thr Gln Ala Thr Thr Pro Ala Pro Lys Val Ala Glu Thr Lys Glu
            180             185             190

Thr Pro Val Ile Asp Gln Asn Ala Thr Thr His Ala Val Lys Ser Gly
        195             200             205

Asp Thr Ile Trp Ala Leu Ser Val Lys Tyr Gly Val Ser Val Gln Asp
    210             215             220

Ile Met Ser Trp Asn Asn Leu Ser Ser Ser Ile Tyr Val Gly Gln
225             230             235             240

Lys Leu Ala Ile Lys Gln Thr Ala Asn Thr Ala Thr Pro Lys Ala Glu
            245             250             255

FIG. 4a

```
Val Lys Thr Glu Ala Pro Ala Ala Glu Lys Gln Ala Ala Pro Val Val
            260             265             270
Lys Glu Asn Thr Asn Thr Asn Thr Ala Thr Thr Glu Lys Lys Glu Thr
            275             280             285
Ala Thr Gln Gln Gln Thr Ala Pro Lys Ala Pro Thr Glu Ala Ala Lys
            290             295             300
Pro Ala Pro Ala Pro Ser Thr Asn Thr Asn Ala Asn Lys Thr Asn Thr
305             310             315             320
Asn Thr Asn Thr Asn Asn Thr Asn Thr Pro Ser Lys Asn Thr Asn Thr
            325             330             335
Asn Ser Asn Thr Asn Thr Asn Thr Asn Ser Asn Thr Asn Ala Asn Gln
            340             345             350
Gly Ser Ser Asn Asn Asn Ser Asn Ser Ser Ala Ser Ala Ile Ile Ala
            355             360             365
Glu Ala Gln Lys His Leu Gly Lys Ala Tyr Ser Trp Gly Gly Asn Gly
            370             375             380
Pro Thr Thr Phe Asp Cys Ser Gly Tyr Thr Lys Tyr Val Phe Ala Lys
385             390             395             400
Ala Gly Ile Ser Leu Pro Arg Thr Ser Gly Ala Gln Tyr Ala Ser Thr
            405             410             415
Thr Arg Ile Ser Glu Ser Gln Ala Lys Pro Gly Asp Leu Val Phe Phe
            420             425             430
Asp Tyr Gly Ser Gly Ile Ser His Val Gly Ile Tyr Val Gly Asn Gly
            435             440             445
Gln Met Ile Asn Ala Gln Asp Asn Gly Val Lys Tyr Asp Asn Ile His
            450             455             460
Gly Ser Gly Trp Gly Lys Tyr Leu Val Gly Phe Gly Arg Val
465             470             475
```

FIG. 4b

Ser Thr Pro Val Val Lys Gln Glu Val Lys Lys
1               5                   10

FIG. 5a

Glu Val Lys Gln Pro Thr Thr Gln Gln Thr Ala Pro Ala
1               5                   10

FIG. 5b

Ala Ile Lys Gln Pro Thr Lys Thr Val Ala Pro Lys
1               5                   10

FIG. 5c

Glu Gln Gln Thr Thr Thr Lys Ala Pro Thr Gln
1               5                   10

FIG. 5d

PROCESSES AND AGENTS FOR DETECTING LISTERIAS

This application is a divisional of application Ser. No. 08/412,227 filed Mar. 27, 1995, now abandoned, which is a continuation of application Ser. No. 08/075,248 filed Jun. 11, 1993, now abandoned.

BACKGROUND OF THE INVENTION

The invention relates to agents and processes for detecting bacteria of the genus Listeria, in particular *L. monocytogenes*.

The members of the genus Listeria are gram-positive rod-shaped bacteria which occur ubiquitously. Seven different species belong to this genus: *L. monocytogenes, L. ivanovii, L. seeligeri, L. welshimeri, L. innocua, L. murrayi* and *L. grayi*. Of these, only *L. monocytogenes* is pathogenic for humans, endangering in particular the newly born, pregnant women and older persons, as well as patients subjected to immunosuppression. *L. monocytogenes* infections frequently have a fatal outcome.

Contaminated foodstuffs, in which the organism can multiply even at low temperatures around 4° C., are frequently the cause of listeria infections. Thus, various listeria epidemics have been attributed to the consumption of contaminated food, such as, for example, raw milk, cheese or coleslaw. Consequently, rapid detection processes for detecting listerias, in particular in foodstuffs or clinical samples, are urgently required. These processes must additionally be able to distinguish between *L. monocytogenes* and the species which are not pathogenic for humans. Furthermore, it must be possible to detect all variants of *L. monocytogenes*, which is the species which is pathogenic for humans. Recent discussions resulted in the proposal to use *L. innocua* as indicator organism for a potential contamination with *L. monocytogenes*. Therefore, the detection of *L. innocua* would be very useful as well.

Detection of *L. monocytogenes* is effected in a known manner using processes which are based on culturing the microorganisms. The process described in Int. J. Food Microbiol. 4 (1987), 249–256 takes two weeks. A somewhat faster process is recommended by the International Dairy Foundation (IDF); however, it takes at least 6–8 days. Both processes are unsuitable for rapid identification because of the time they take. In addition, both processes are labor-intensive, since nutrient media must be inoculated repeatedly in order to obtain single colonies, and since the isolates must subsequently be characterized using biochemical and serological methods of investigation.

While the immunological tests which are currently on the market only take a few hours, they do not permit the important differentiation between different species of listerias. In these processes, also, a two-day pre-enrichment cultivation is required.

A method is described in Appl. Environ. Microbiol. 54 (1988), 2933–2937 in which *L. monocytogenes* is specifically detected using synthetic oligodeoxyribonucleotide probes. However, the probes which are used are not sufficiently specific, since they also react with the species *L. seeligeri*, which is not pathogenic for humans. Prior multiplication of the organisms is required for this process as well: samples of foodstuffs, or their dilutions, are spread on agar plates, and then the inoculated plates are incubated and subsequently investigated by the colony hybridization procedure using a radioactively labelled DNA probe. Detection takes place by autoradiography. This method, too, is labor-intensive and time-consuming.

The DNA sequence of the iap (invasion-associated protein) gene of *L. monocytogenes* is described in Infect. Immun. 58, 1943–1950 (1990). This gene encodes a protein which is also known under the designation p60 and which occurs in variants in all Listeria species. In *L. monocytogenes* this protein is responsible for the ability to invade animal cells. A polynucleotide (400 bases) having a component sequence from this gene is suitable as a DNA probe for distinguishing *L. monocytogenes* from other organisms.

The polymerase chain reaction (PCR) permits the in vitro amplification of nucleic acids, and prior cultivation is generally not necessary when using this process. In order to start the reaction, short nucleic acid fragments (primers) are required, which primers encompass the section of the genome which is to be amplified. Usually, two primers are required, each of which hybridizes with one nucleic acid strand. One of the primers therefore possesses the complementary sequence to the relevant section of the gene. The choice of these primers determines the specificity of the detection reaction. The use of this process for detecting *L. monocytogenes* is described in Appl. Environmental Microbiology 57, 606–609 (1991), in Letters Appl. Microbiol. 11, 158–162 (1990) and in J. Appl. Bact. 70, 372–379 (1991). More extensive information regarding the details of these processes is available in these publications. The DNA primers bind to the gene for listeriolysin, the listeria hemolysin. The specificity of these primers is at least uncertain as is evident from comments in J. Appl. Bact. 70: *L. seeligeri* cannot be differentiated with certainty from *L. monocytogenes*. The unambiguous detection of *L. monocytogenes* has thus hitherto not been possible using the PCR technique.

Polyclonal antibodies against *L. monocytogenes* p60 also react with the p60 protein of other, non-pathogenic Listeria species. Such antibodies are therefore unsuitable for specifically detecting *L. monocytogenes* by immunological processes. It is possible in principle to purify a polyvalent antiserum of this nature by the specific absorption of interfering antibody fractions: for this purpose, p60 protein from all the other Listeria species is covalently bound to carriers. The unwanted antibody fractions can be specifically absorbed; an antiserum then remains which only reacts with p60 protein from *L. monocytogenes*. This method for obtaining an *L. monocytogenes*-specific serum is elaborate: substantial quantities of the polyvalent antiserum are required as starting material, as are, in addition, the p60 iap gene products of the different Listeria species. The obtention of monoclonal antibodies against. p60 protein would not be associated with this large material requirement; nevertheless, the raising of antibodies against particular epitopes depends on chance: it is first of all necessary to prepare a large number of antibody-producing cell clones, from which suitable clones must then be selected. It has thus far not been possible to obtain antibodies in a targeted manner against epitopes which are specific for *L. monocytogenes*. The same holds true for epitopes which are specific for *L. innocua*.

SUMMARY OF THE INVENTION

It is the object of the present invention to provide improved agents and methods for differentiating bacteria, of the genus Listeria, in particular for detecting bacteria of the species *L. monocytogenes*. In particular, primer sequences which are suitable for the PCR technique are provided according to the invention, as are peptides for the targeted production of specific antibodies which are suitable for the immunological detection of the species *L. monocytogenes* and *L. innocua*.

Upon further study of the specification and appended claims, further objects and advantages of this invention will become apparent to those skilled in the art.

The invention relates to primers, selected from the iap gene, for the amplification of nucleic acids, for example by means of the polymerase chain reaction, characterized in that the primers contain, as a component sequence, at least one sequence according to one of the formulae Ia to Ih and/or an affiliated complementary sequence, it being possible for up to 20 further nucleotide moieties to be bound in front of and/or behind this component sequence Such primers are suitable for detecting and differentiating bacteria of the genus Listeria, including in particular the species *L. monocytogenes*, by means of PCR.

AATATGAAAAAAGC(SEQ ID NO:1) Ia
GCTTCGGTCGCGTA(SEQ ID NO:2) Ib
ACAGCTGGGATTGC(SEQ ID NO:3) Ic
ACTGCTAACACAGCT(SEQ ID NO:4) Id
TAACAGCAATTCAAG(SEQ ID NO:5) Ie
CTGAGGTAGCGAGC(SEQ ID NO:6) If
AGCACTCCAGTTGTTA(SEQ ID NO:7) Ig
GCAGTTTCTAAACCT(SEQ ID NO:8) Ih

In this context, primers are particularly preferred which contain a sequence according to one of the formulae IIa to IIh and/or an affiliated complementary sequence.

ATGAATATGAAAAAAAGCAAC(SEQ ID NO:9) IIa
TTGGCTTCGGTCGCGTATAA(SEQ ID NO:10) IIb
GCTACAGCTGGGATTGCGGT(SEQ ID NO:11) IIc
CAAACTGCTAACACAGCTACT(SEQ ID NO:12) IId
CAATAACAGCAATTCAAGTGC(SEQ ID NO:13) IIe
TAACTGAGGTAGCGAGCGAA(SEQ ID NO:14) IIf
ACTAGCACTCCAGTTGTTAAAC(SEQ ID NO:15) IIg
CCAGCAGTTTCTAAACCTGCT(SEQ ID NO:16) IIh

The invention additionally relates to peptides which contain, as a component sequence, at least one sequence according to one of the formulae IIIa to IIIi, it being possible for in each case up to seven amino acids to be bound by peptide linkages in front of and/or behind this component sequence.

ProValAlaProThrGln(SEQ ID NO:17) IIIa
ThrGlnAlaThrThrProAla(SEQ ID NO:18) IIIb
AlaIleLysGlnThrAlaAsnThrAla(SEQ ID NO:19) IIIc
GlnGlnThrAlaProLysAlaProThr(SEQ ID NO:20) IIId
ValAsnAsnGluValAlaAlaAlaGluLysThrGlu(SEQ ID NO:21) IIIe
ThrProValValLysGlnGluValLys(SEQ ID NO:22) IIIf
ValLysGlnProThrThrGlnGlnThrAlaPro(SEQ ID NO:23) IIIg
IleLysGlnProThrLysThrValAlaPro(SEQ ID NO:24) IIIh
GlnGlnThrThrThrLysAlaProThr(SEQ ID NO:25) IIIi

In this context, peptides are particularly preferred which have a sequence according to one of the FIGS. 2*a–i*(SEQ ID NO:26–34, respectively), and FIGS. 5*a–d*(SEQ ID NO:35–38, respectively).

The invention also relates to the use of one of the said peptides, having a component sequence according to one of the formulae IIIa to IIIi, for preparing immunogenic conjugates. Peptides having a sequence according to one of the FIGS. 2*a–i* and of the FIGS. 5*a–d* are particularly preferred for this purpose.

The invention also relates to an antibody which binds an epitope which is formed from the polypeptide according to FIG. 3(SEQ ID NO:39) or contains a peptide according to one of the formulae IIIa–IIIi, preferably according to one of the FIGS. 2*a–i* and of FIGS. 5*a–d*.

The invention further relates to an antibody which can be prepared by immunizing an experimental animal with a polypeptide according to FIG. 3 or with an immunogenic conjugate which contains a peptide having 7 to 24 amino acids selected from the polypeptide according to FIG. 3.

The invention also relates to a process for preparing an antibody directed against the p60 protein from listerias by immunizing an experimental animal with an immunogen and isolating the antibodies, characterized in that a polypeptide according to FIG. 3 or an immunogenic conjugate which contains a polypeptide according to FIG. 3 is used as the immunogen. In this context, immunogenic conjugates are preferred which contain a peptide having 7 to 24 amino acids selected from the polypeptide according to FIG. 3, or which contain a peptide according to one of the formulae IVa–IVi, in which $X^3$ and $X^4$ are each independently of one another hydrogen, an arbitrary amino acid or an arbitrary oligopeptide having up to 7 amino acids.

$X^3$ProValAlaProThrGln$X^4$(SEQ ID NO:17) IVa
$X^3$ThrGlnAlaThrThrProAla$X^4$(SEQ ID NO:18) IVb
$X^3$AlaIleLysGlnThrAlaAsnThrAla$X^4$(SEQ ID NO:19) IVc
$X^3$GlnGlnThrAlaProLysAlaProThr$X^4$(SEQ ID NO:20) IVd
$X^3$ValAsnAsnGluValAlaAlaAlaGluLysThrGlu$X^4$(SEQ ID NO:21) IVe
$X^3$ThrProValValLysGlnGluValLys$X^4$(SEQ ID NO:22) IVf
$X^3$ValLysGlnProThrThrGlnGlnThrAlaPro$X^4$(SEQ ID NO:23) IVg
$X^3$IleLysGlnProThrLysThrValAlaPro$X^4$(SEQ ID NO:24) IVh
$X^3$GlnGlnThrThrThrLysAlaProThr$X^4$(SEQ ID NO:25) IVi

Especially preferred are peptides having a sequence according to one of the FIGS. 2*a–i* or 5*a–d*.

The invention further relates to the use of a primer, which contains a component sequence according to one of the formulae Ia–Ih or preferably a sequence according to one of the formulae IIa–IIh or an affiliated complementary sequence, for detecting bacteria of the genus Listeria.

The invention also relates to processes for detecting bacteria of the genus Listeria by means of a primer which contains a component sequence according to one of the formulae Ia–Ih or preferably a sequence according to one of the formulae IIa–IIh or an affiliated complementary sequence.

The invention further relates to the use of an antibody which is directed against an epitope from the polypeptide sequence according to FIG. 3, or which is directed against one of the epitopes having an amino acid sequence according to one of the FIGS. 2*a–i* or of the FIGS. 5*a–d*, for detecting bacteria of the genus Listeria.

The invention also relates to processes for detecting bacteria of the genus Listeria by means of an antibody which is directed against an epitope from the polypeptide sequence according to FIG. 3, or which is directed against one of the epitopes having an amino acid sequence according to one of the FIGS. 2*a–i*, or to one of the FIGS. 5*a–d*.

The invention finally relates to test kits for detecting bacteria of the genus Listeria, in particular of the species *L.*

*monocytogenes*, by means of the amplification of nucleic acids, for example by means of the polymerase chain reaction, which contain a primer having a component sequence according to one of the formulae Ia–Ih or preferably having a sequence according to one of the formulae IIa–IIh, or an affiliated complementary sequence.

The invention furthermore relates to test kits for the immunological detection of bacteria of the species *Listeria monocytogenes*, in which an antibody which is directed against an epitope from the polypeptide sequence according to FIG. 3, or which is directed against one of the epitopes having an amino acid sequence according to one of the FIGS. 2a–i, is contained, as well as to test kits for the immunological detection of bacteria of the species *Listeria innocua*, in which an antibody, which is directed against an epitope having an amino acid sequence according to one of the FIGS. 5a–d is contained.

BRIEF DESCRIPTION OF THE DRAWINGS

Various other objects, features and attendant advantages of the present invention will be more fully appreciated as the same becomes better understood when considered in conjunction with the accompanying drawing, in which like reference characters designate the same or similar parts throughout the several views, and wherein:

FIGS. 2a–i show the amino acid sequences (SEQ ID NO:26–34 respectively) of the particularly preferred imnmunogenic peptides selected from the sequence of the p60 protein from *Listeria monocytogenes*.

FIG. 3 shows the amino acid sequence (SEQ ID NO:39) of the polypeptide selected from the sequence of the p60 protein from *Listeria monocytogenes*, whose epitopes are suitable for the immunological detection of bacteria of the genus Listeria.

FIGS. 4A and 4B show, for comparative purposes, the amino acid sequence (SEQ ID NO:40) of the p60 protein from *Listeria monocytogenes*, which is presented in two component FIGS. a and b.

FIGS. 5a–d show the amino acid sequences (SEQ ID NO:35–38 respectively), of the particularly preferred immunogenic peptides selected from the sequence of protein p60 from *Listeria innocua*.

Figure 1:
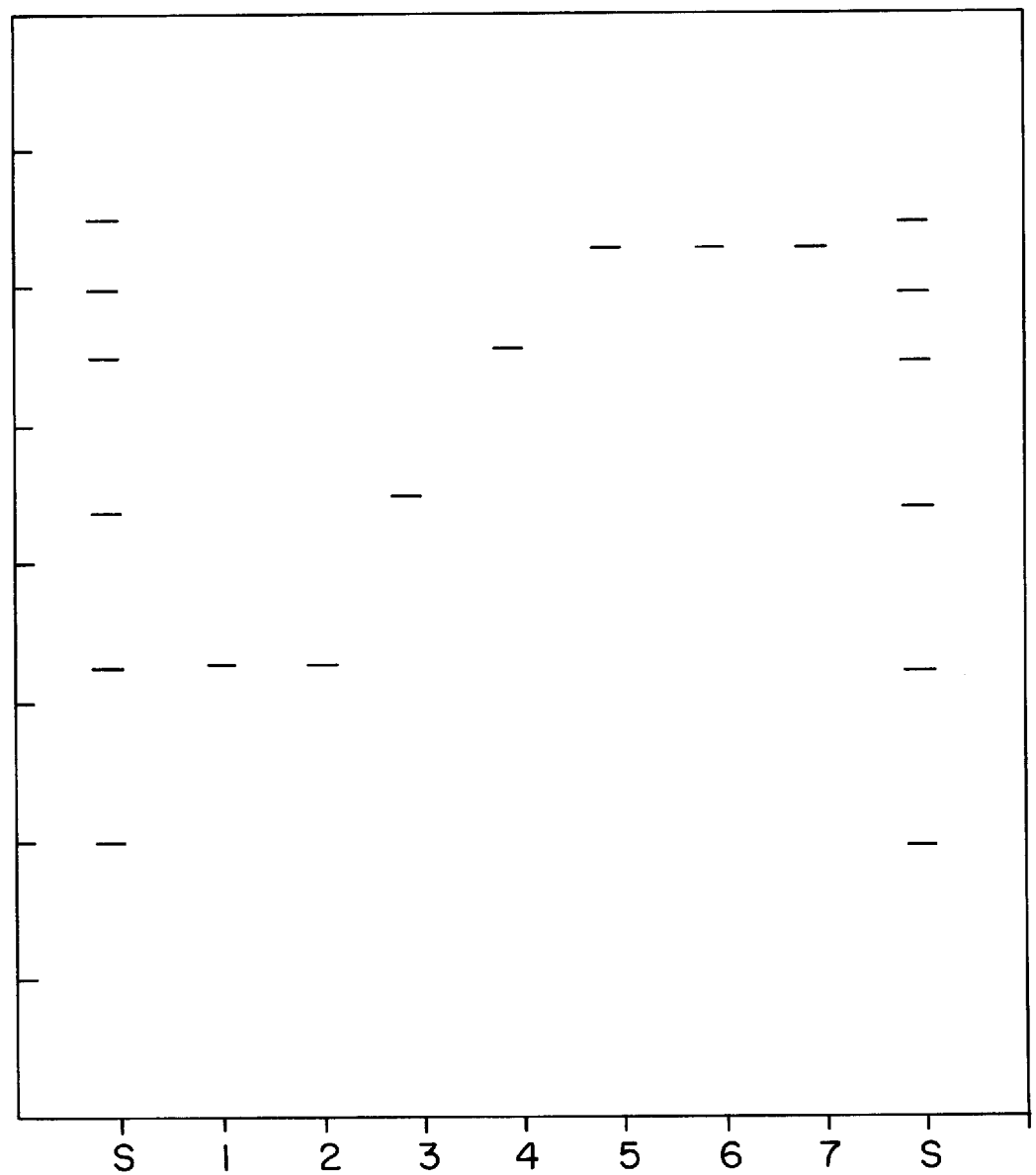
FIG. 1 shows the result of the electrophoretic separation of amplification products; the experimental details are presented in Example 8.

The invention is described below in more detail. In this context, the details of biochemical, immunological and molecular biological processes, which are known to the person skilled in the art and whose details are described in the literature, are presumed. In these processes, use can also be made of variations which are known per se but which are not described in detail here.

The oligonucleotides according to the invention described by the formulae Ia–Ih and IIa–IIh are suitable as primers for nucleic acid amplification methods, and thus for the specific detection of bacteria of the genus Listeria. Their sequences are presented in the customary manner, i.e., written from the 5' end to the 3' end. Depending on the requirements of the amplification system being used on any particular occasion, either deoxyribonucleotides or ribonucleotides having the sequences according to the invention are employed. In the latter case, the thyridine moieties are on each occasion replaced by uridine moieties. It is further known to the person skilled in the art that frequently the exchange of one or of a few bases in a nucleic acid sequence does not alter its biological properties. For this reason, the nucleotide sequences according to the invention also comprise those which are derived by base exchange from the sequences Ia–Ih and IIa–IIh, and which biologically show the same effect as the respective primer having the original sequence. Since normally one primer should in each case react with one of the DNA strands, one of the primers is employed in the complementary sequence. The complementary sequence is obtained in a known manner according to the rules for base pairing.

Based on the respective sequence, the oligonucleotides according to the invention can be synthesized by processes known to the person skilled in the art, for example by the phosphotriester or the phosphoamidite method. The phosphoamidite method is preferably employed, in particular using mechanized synthesizers. The method is described in Tetrahedron Lett. (1981) 22:1859–1862. Further details of synthetic processes of this nature are described, for example, in Winnacker, E. L. (1985) Gene und Klone [Genes and Clones], page 44–61 (VCH-Verlagsgesellschaft mbH, Weinheim).

The primers according to the invention are suitable for DNA amplification, for example using the polymerase chain reaction (PCR). For this purpose, the DNA is first dissociated into the single strands by heating. Two primers are used which in each case hybridize with the homologous DNA segment on one of the DNA strands in each case. The genome segment which lies between these two primers is amplified. The primers attached to the DNA represent the starting points for the amplification. A polymerase, preferably Taq DNA polymerase, subsequently completes, in the presence of the four nucleoside triphosphates, the second strand corresponding to the sequence of the original DNA. Subsequently, the double strands which have arisen are dissociated once again into the single strands by heating. This amplification cycle can be repeated a number of times. After a sufficient number of amplification cycles, the amplified nucleic acid can be detected by means of known methods. For this purpose, the DNA can be separated by means of electrophoresis, and subsequently stained with ethidium bromide, and finally detected by fluorescence using UV excitation. Detection using DNA hybridization is also possible. The details of suitable amplification and detection methods are also described in review articles, e.g., Innis et al. (eds.), PCR Protocols (Academic Press, Inc., Harcourt Brace Jovanovich, Publishers). Other nucleic acid amplification processes in which the primers according to the invention can be used are also known from the literature. These include the ligase chain reaction, described by Bond, S. et al. ((1990), pp. 425–434, Raven Press (New York, N.Y./USA)).

The selection of the primers according to the preferred formulae IIa–IIh determines the position of the start points on the iap gene, and thus the specificity of the detection reaction: thus, combinations of primers selected from the sequence of the iap gene proved to be unspecific, and consequently unsuitable for detecting listerias by means of DNA amplification (in this connection see, for example, column F in Table 1). However, other selected combinations proved to be specific for the genus Listeria, others for groups of Listeria species, and others again for individual Listeria species. Altogether, therefore, the selection and the composition of the primers is critical. The selection of one of the two primers is always particularly critical, while the second primer can be more easily varied without significantly altering the specificity of the detection reaction. Consequently, according to the teaching of the present invention, for this second primer, a sequence can perfectly well be chosen which does not correspond to one of the formulae Ia–Ih or IIa–IIh.

According to the invention, at least one of the primers is selected from the formulae Ia–Ih or preferably from the formulae IIa–IIh. As already explained, the second primer has substantially less influence than the first primer on the specificity of the amplification reaction. However, combinations are preferred in which both primers are selected from the formulae Ia–Ih or IIa–IIh. Examples of preferred combinations of this nature are (typical results are summarized in Table 1):

a) When using a combination of a primer according to formula IIc with a primer with the complementary sequence according to formula IIb, only the DNA of listerias is amplified, and not the DNA of other types of bacteria (see column D in Table 1).

b) When using a combination of a primer according to formula IId with a primer with the complementary sequence according to formula IIb, only the DNA of *L. monocytogenes* is amplified, and not the DNA of other listerias or other bacteria (see column B in Table 1).

c) When using a combination of a primer according to formula IIf with a primer with the complementary sequence according to formula IIb, only the DNA of particular Listeria species is amplified, namely that of *L. seeligeri, L. welshimeri* and *L. ivanovii*, exclusively. This consequently permits group-specific detection (see column E in Table 1).

d) Another example of group-specific detection consists in the use of a combination of a primer according to formula IIh with a primer with the complementary sequence according to formula IIb: only the DNA of *L. grayi* and *L. murrayi* is amplified (see column G in Table 1).

e) Since the amplification products of different Listeria species exhibit varying molecular weights, bacteria of the genus Listeria can be differentiated by a combination of several primers (according to formulae IId, IIf, IIg and IIh) with the complementary sequence of formula IIb using one single polymerase reaction. Details of this further development of the polymerase technique are evident from Example 8 (see column H in Table 1, as well as FIG. 1).

As already mentioned, it is also possible to detect the amplification products by nucleic acid hybridization. To do this, suitable nucleic acid fragments (nucleic acid probes) are added to the reaction mixture after the amplification. These nucleic acid probes possess a base sequence which is completely or partially complementary to the amplified gene segment. In addition, these probes are labelled for a detection reaction: they can contain radioactive isotopes, or carry fluorescent labels, or else be labelled by enzymes. Suitable labelling agents, methods for their introduction into the nucleic acid probe, and detection methods, are known to the person skilled in the art.

In particular, the amplification reaction can be designed specifically for the genus Listeria (as described in more detail above under a)) or for a group of Listeria species (as described above under c) and d)) By using nucleic acid probes which are in each case specific for one species, the presence of these species of Listeria can then be discerned in the reaction mixture. If the probes contain different labelling agents, different species can also be detected side by side. This variation of the process consequently permits, in a similar manner to that described above under e), the detection of different Listeria species side by side.

The use of a nucleic acid probe, or of a mixture of different probes, which react with amplification products of all the Listeria species makes it possible to check the specificity of the amplification reaction or to prepare a unitary detection reagent for different Listeria species.

The peptides according to the invention, according to formulae IVa–IVi and according to FIGS. 2a–i or to FIGS. 5a–d, can be incorporated into immunogenic conjugates. Using these conjugates, antibodies can be produced which make it possible specifically to detect bacteria of the genus Listeria using immunological methods.

The positions of the peptides according to the invention in the overall sequence of the p60 protein from *Listeria monocytogenes* are given below:

a) The sequence according to formula IIIa begins with proline at position 148 of the p60 sequence (FIG. 4a); the peptides according to FIGS. 2a, 2e and 2f are also located in this region.

b) The sequence according to formula IIIb begins with threonine at position 178 of the p60 sequence (FIG. 4a); the peptides according to FIGS. 2b and 2h are also located in this region.

c) The sequence according to formula IIc begins with alanine at position 243 of the p60 sequence (FIG. 4a); the peptides according to FIGS. 2c and 2i are also located in this region.

d) The sequence according to formula IIId begins with glutamine at position 292 of the p60 sequence (FIG. 4b); the peptide according to FIG. 2d is also located in this region.

e) The sequence according to formula IIe begins with valine at position 71 of the p60 sequence (FIG. 4a); the peptide according to FIG. 2g is also located in this region.

The sequences of the peptides according to the invention which are shown in FIGS. 5a–d are derived from the total sequence of protein p60 from *Listeria innocua;* the same holds true for the partial sequences shown in formula IIIf–i and IVf–i.

It is known to the person skilled in the art that the exchange of one or of a few amino acids in a peptide frequently does not alter its biological properties. For this reason, the peptide sequences according to the invention also comprise those which are derived, by amino acid exchange, from the sequences according to FIGS. 2a–i, according to FIGS. 5a–d, or according to FIG. 3, and which biologically show the same effect as the respective peptides having the original sequence. One of skill in the art can routinely determine preferred exchanges in accordance with substitutions generally recognized as being preferred, e.g., according to the groups outlined in Dayhoff, M. O., *Atlas of Protein Sequence and Structure,* Vol. 5, p. 98 (1972), and updates thereof.

The selection of the peptides according to the invention proves to be critical. For example, when a particular peptide, ThrAsnThrAsnThrAsnThrAsnThrAsnThrAsn(SEQ ID NO:41)

which is encoded by a gene segment around nucleotide 1390 which is specific for *L. monocytogenes,* was selected for the production of antibodies, none of the antisera, surprisingly, showed a reaction with the p60 protein.

Based on the sequence of the amino acids, the peptides can be synthesized by processes which are known to the person skilled in the art, for example by the $t_{boc}$ or by the $f_{moc}$ (tert-butyloxycarbonyl, or 9-fluorenylmethyloxycarbonyl) processes. Details of these processes are described, for example, in J. Am. Chem. Soc. 85, 2149–2154 (1963) and in Synthetic Polypeptides as Antigens (van Regenmortel et al. (eds.), Elsevier 1988 (volume 19 of the series Laboratory Techniques in Biochemistry and Molecular Biology). The $f_{moc}$ process is preferred, in particular mechanized process variations thereof. Details of the process, as well as suitable amino acid protective groups, are known to the person skilled in the art.

Peptides are generally not suitable for producing antibodies. However, if peptides are coupled to high-molecular weight carrier substances, immunogenic conjugates are formed. The peptides according to the invention can be conjugated with known carrier substances. Among these are polyethylene glycols, serum albumins, KLH (keyhole limpet hemocyanin), ovalbumin, glucose dehydrogenase from *Bacillus megaterium* and PPD (purified protein derivative of tuberculin). Preferred carrier substances are KLH and glucose dehydrogenase from *B. megaterium*.

Besides this, bridging compounds (linkers) are frequently employed as well. These are low-molecular weight organic compounds having at least two linkable functional groups. Suitable compounds are known to the person skilled in the art; among these are, for example, 1,2-diaminoethane, succinic acid, β-alanine, 1,6-diaminohexane, 6-aminocaproic acid, adipic acid and cysteine. Cysteine is preferably employed as the linker, with this amino acid residue being incorporated during the synthesis of the peptide. Linkers which contain both an amino and a carboxyl function (e.g., β-alanine, 6-aminocaproic acid or cysteine), can be linked either at the C-terminus or at the N-terminus of the peptide. m-Maleimidobenzoic acid N-hydroxysuccinimide ester (MBS) is preferably employed for preparing the bonds between the peptide and the carrier substance.

The said immunogenic conjugates serve to produce antibodies in experimental animals according to known processes. Usually, mammals are used for this purpose, for example sheep, goats, rabbits or mice. Rabbits are preferred for producing polyclonal antibodies. However, it is also possible to produce monoclonal antibodies using the immunogenic conjugates according to the invention.

Details of the immunological processes are known to the person skilled in the art. In addition, instructions for carrying out these processes are readily available in the literature; the following may be mentioned by way of example:

Antibodies, E. Harlow and D. Lane, Cold Spring Harbor (1988)

Woodard, L. F. and Jasman, R. L. (1985) Vaccine 3, 137–144

Woodard, L. F. (1989) Laboratory Animal Sci. 39, 222–225

Handbook of Experimental Immunology, Weir, D. M. et al. eds. (1986): Blackwell Scientific Publications, Oxford, GB.

Among these processes are, for example, the conjugation and immunization processes, as well the preparation and purification of antibodies, and also immunological detection processes. The immunological detection processes in which antibodies according to the invention can be used include preferably agglutination processes, immunometric detection processes, the immmunoblot processes and in particular the sandwich ELISA processes.

According to the invention, the concept antibodies embraces both immunoglobulins and antisera. It is furthermore known to the person skilled in the art that, instead of a single antibody which is directed against a single epitope, a mixture of different antibodies of differing specificity may frequently be used. This results in advantages, in particular with regard to the sensitivity of detection. This applies in particular to monoclonal antibodies, but also to other antibodies, which are in each case directed against one epitope. Correspondingly, it can be advantageous to combine a plurality of antibodies which are directed against different peptide structures according to the formulae III-a–IIIi or according to one of the FIGS. 3, 2a–i or 5a–d, for the use according to the invention and/or the processes according to the invention.

Details regarding the preparation of the primers and peptides according to the invention, as well as of their use, are evident from the following examples. The person skilled in the art will elicit further methodological details from the cited literature. The examples are intended to illustrate the subject of the invention, and do not represent any limitation of the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German applications P 42 19 111.4 and P 42 39 567.4, are hereby incorporated by reference.

EXAMPLES

Example 1

Preparation of the primer according to formula IIa

The primer according to formula IIa is prepared by the phosphoamidite method using the 380A DNA synthesizer from Applied Biosystems. The essential features of the method are described in Tetrahedron Lett. (1981) 22:1859–1862. Further details can be found in the literature supplied by the instrument manufacturer.

The primers according to formula IIc, IId, IIf, IIg and IIh are prepared in a corresponding manner. The primers according to formula IIb and IIe are prepared in the respective complementary sequence (IIb: TTGGCTTCGGTCGCGTAGAATTCATA;(SEQ ID NO:10);

IIe: GCACTTGAATTGCTGTTATTG)(SEQ ID NO:43).

Example 2

Performance of the PCR reaction for the species-specific detection of *L. monocytogenes*

A sample of bacteria containing about 1µg of DNA, is suspended in 50 µl of buffer (10 mM Tris-HCl pH 8.5; 1.5 mM $MgCl_2$ and 50 mM KCl) and heated at 110° C. for 5 minutes. Subsequently, primers according to formula IId and IIe (see Example 1; in each case 0.4 µg), and 2.5U of Taq polymerase (from Pharmacia), dissolved in reaction buffer (10 mM Tris-HCl pH 8.5; 1.5 mnM $MgCl_2$ and 50 mM KCl), and in each case 200 µmol of dGTP, DATP, dTTP and dCTP are added (total reaction volume 100 µl). The first denaturation step lasts for 3 minutes at 94° C.

Subsequently, the reaction mixture is maintained at a temperature of 55° C. for 30 seconds (annealing phase), and at a temperature of 72° C. for one minute (elongation phase). The subsequent denaturation steps (at 94° C.) last for 45 seconds. After 30 reaction cycles, a concluding elongation step (at 72° C.), of 5-minute duration, is carried out.

The PCR products are separated on a polyacrylamide gel (6%) in a running buffer of Tris-borate (in each case 50 mM) containing EDTA (2.5 mM). Subsequently, the separated PCR products are stained with ethidium bromide (0.1 mg/ml in water), and visualized by irradiation with UV light (260 nm).

PCR products are only observed (see column A in Table 1) if DNA or cells from *L. monocytogenes* are present in the sample.

Example 3

Performance of the PCR reaction for the species-specific detection of *L. monocytogenes*

The process described in Example 2 is repeated using primers according to formula IId and IIb (see Example 1) instead of the primers according to formula IId and IIe. In this case, too. PCR products are only observed if DNA or cells from *L. monocytogentes* are present in the sample (see column B in Table 1).

TABLE 1

Specificity of the polymerase chain reaction using different primers corresponding to formula IIa-IIh

| Combination: | A | B | C | D | E | F | G | H |
|---|---|---|---|---|---|---|---|---|
| Primer 1: | IId | IId | IIg | IIc | IIf | IIa | IIh | M[3)] |
| Primer 2:[1)] | IIe | IIb | IIb | IIb | IIb | IIb | IIb | IIb |
| Reaction investigated Bacteria: | | | | | | | | |
| *L. monocytogenes* | | | | | | | | |
| serovar 1/2a EDG | + | + | − | + | − | + | − | + |
| serovar 1/2a Mack.[2)] | + | + | − | + | − | + | − | + |
| serovar 1/2b | + | + | − | + | − | + | − | + |
| serovar 1/2c | + | + | − | + | − | + | − | + |
| serovar 3a | + | + | − | + | − | + | − | + |
| serovar 3b | + | + | − | + | − | + | − | + |
| serovar 3c | + | + | − | + | − | + | − | + |
| serovar 4a | + | + | − | + | − | + | − | + |
| serovar 4ab | + | + | − | + | − | + | − | + |
| serovar 4b | + | + | − | + | − | + | − | + |
| serovar 4c | + | + | − | + | − | + | − | + |
| serovar 4d | + | + | − | + | − | + | − | + |
| serovar 4e | + | + | − | + | − | + | − | + |
| serovar 7 | + | + | − | + | − | + | − | + |
| *L. ivanovii* | − | − | − | + | + | + | − | + |
| *L. seeligeri* | − | − | − | + | + | + | − | + |
| *L. innocua* | | | | | | | | |
| serovar 6a | − | − | + | + | − | + | − | + |
| serovar 6b | − | − | + | + | − | + | − | + |
| serovar 4ab | − | − | + | + | − | + | − | + |
| *L. welshimeri* | − | − | − | + | + | + | − | + |
| *L. murrayi* | − | − | − | + | − | + | + | + |
| *L. grayi* | − | − | − | + | − | + | + | + |
| *Enterococcus faecalis* | − | − | − | − | − | + | − | − |
| *Bacillus cereus* | − | − | − | − | − | + | − | − |
| *Micrococcus flavus* | − | − | − | − | − | + | − | − |

Legend:
+ PCR product detected
− no PCR product detectable
[1)]Complementary sequence
[2)]Mack.: mackaness strain
[3)]M: Mixture of primers according to formula IId, IIf, IIg and IIh; Amplification products can be differentiated on the basis of the molecular weight.

Example 4

Performance of the PCR reaction for the genus-specific detection of bacteria of the genus Listeria A sample of bacteria containing about 1 µg of DNA, is suspended in 50 µl water and heated at 110° C. for 5 minutes. Subsequently, primers according to formula IIc and IIb (see Example 1; in each case 0.4 µg), and 2.5U of Taq polymerase (from Pharmacia), dissolved in reaction buffer (10 mM Tris-HCl pH 8.5; 1.5 mM MgCl$_2$ and 50 mM KCl), and in each case 200 µmol of dGTP, dATP, dTTP and dCTP are added (total reaction volume 100 µl). The first denaturation step lasts for 3 minutes at 9° C. Subsequently, the reaction mixture is maintained at a temperature of 56° C. for 30 seconds (annealing phase), and at a temperature of 72° C. for 2 minutes (elongation phase). The subsequent denaturation steps (at 94° C.) each last for 45 seconds. After 30 reaction cycles, a concluding elongation step (at 72° C.), of 5-minute duration, is carried out.

The PCR products are separated on an agarose gel (1 %) in a running buffer of Tris-borate (in each case 50 mM) containing EDTA (2.5 mM). Subsequently, the separated PCR products are stained by staining with ethidium bromide (0.1 mg/ml in water), and visualized by irradiation with UV light (260 nm).

In this case, PCR products are observed if DNA or cells from bacteria of the genus Listeria are present in the sample (see column D in Table 1).

Example 5

Performance of the PCR reaction for the group-specific detection of *listerias*

A sample of bacteria containing about 1 µg of DNA, is suspended in 50 µl water and heated at 110° C. for 5 minutes. Subsequently, primers according to formula IIf and IIb (see Example 1; in each case 0.4 µg), and 2.5U of Taq polymerase (from Pharmacia), dissolved in reaction buffer (10 mM Tris-HCl pH 8.5; 1.5 mM MgCl$_2$ and 50 mM KCl), and in each case 200 µmol of dGTP, dATP, dTTP and dCTP are added (total reaction volume 100 µl). The first denaturation step lasts for 3 minutes at 94° C. Subsequently, the reaction mixture is maintained at a temperature of 58° C. for 45 seconds (annealing phase), and at a temperature of 72° C. for one minute (elongation phase). The subsequent denaturation steps (at 94° C.) last for 45 seconds. After 30 reaction cycles, a concluding elongation step (at 72° C.). of 5-minute duration, is carried out.

The PCR products are separated on an agarose gel (1%) in a running buffer of Tris-borate (in each case 50 mM) containing EDTA (2.5 mM). Subsequently, the separated PCR products are stained by staining with ethidium bromide (0.1 mg/ml in water), and visualized by irradiation with UV light (260 nm).

In this case, PCR products are observed only if DNA or cells of bacteria from the group *L. ivanovii*, *L. seeligeri* and *L. welshimeri* are present in the sample (see column E in Table 1).

Example 6

Performance of the PCR reaction for the species-specific detection of *L. innocua*

A sample of bacteria containing about 1 µg of DNA, is suspended in 50 µl of buffer (10 mM Tris-HCl pH 8.5; 1.5 mM MgCl$_2$ and 50 mM KCl) and heated at 110° C. for 5 minutes. Subsequently, primers according to formula IIg and IIb (see Example 1; in each case 0.4 µg), and 2.5U of Taq polymerase (from Pharmacia), dissolved in reaction buffer (10 mM Tris-HCl pH 8.5; 1.5 mM MgCl$_2$ and 50 mM KCl), and in each case 200 µmol of dGTP, DATP, dTTP and dCTP are added (total reaction volume 100 µl). The first denaturation step lasts for 3 minutes at 94° C. Subsequently, the reaction mixture is maintained at a temperature of 62° C. for 60 seconds (annealing phase), and at a temperature of 72° C. for 45 seconds (elongation phase). The subsequent denaturation steps (at 94° C.) last for 45 seconds. After 30 reaction cycles, a concluding elongation step (at 72° C.), of 5-minute duration, is carried out.

The PCR products are separated on an agarose gel (1%) in a running buffer of Tris-borate (in each case 50 mM)

containing EDTA (2.5 mM). Subsequently, the separated PCR products are stained by staining with ethidium bromide (0.1 mg/ml in water), and visualized by irradiation with UV light (260 mn).

PCR products are only observed if DNA or cells of *L. innocua* are present in the sample (see column C in Table 1).

Example 7

Performance of the PCR reaction for the group-specific detection of *listerias*

A sample of bacteria containing about 1 µg of DNA, is suspended in 50 µl of water and heated at 110° C. for 5 minutes. Subsequently, primers according to formula IIh and IIb (see Example 1; in each case 0.4 µg), and 2.5U of Taq polymerase (from Pharmacia), dissolved in reaction buffer (10 mM Tris-HCl pH 8.5; 1.5 mM MgCl$_2$ and 50 mM KCl), and in each case 200 µmol of dGTP, dATP, dTTP and dCTP, are added (total reaction volume 100 µl). The first denaturation step lasts for 3 minutes at 94° C. Subsequently, the reaction mixture is maintained at a temperature of 56° C. for 45 seconds (annealing phase), and at a temperature of 72° C. for 45 seconds (elongation phase). The subsequent denaturation steps (at 94° C.) last for 45 seconds. After 30 reaction cycles, a concluding elongation step (at 72° C.), of 5-minute duration, is carried out.

The PCR products are separated on an agarose gel (1%) in a running buffer of Tris-borate (in each case 50 mM) containing EDTA (2.5 mM). Subsequently, the separated PCR products are stained by staining with ethidium bromide (0.1 mg/ml in water) and visualized by irradiation with UV light (260 nm).

In this case, PCR products are only observed if DNA or cells of bacteria from the group *L. grayi* and *L. murrayi* are present in the sample (see column G in Table 1).

Example 8

Performance of a combined PCR reaction for the species-specific detection of *L. monocytogenes* and of *L. innocua* and for the group-specific detection of the groups *L. ivanovii/L. seeligeri/L. welshimeri* and *L. grayi/L. murrayi*

A sample of bacteria containing about 1 µg of DNA, is suspended in 50 µl of buffer (10 mM Tris-HCl pH 8.5; 1.5 mM MgCl$_2$ and 50 mM KCl) and heated at 110° C. for 5 minutes. Subsequently, a mixture of primers according to formula IId, IIf, IIg, IIh and IIb (see Example 1; in each case 0.4 µg), as well as 2.5U of Taq polymerase (from Pharmacia), dissolved in reaction buffer (10 mM Tris-HCl pH 8.5; 1.5 mM MgCl$_2$ and 50 mM KCl), and in each case 200 µmol of dGTP, dATP, dTTP and dCTP, are added (total reaction volume 100 µl). The first denaturation step lasts for 3 minutes at 94° C. Subsequently, the reaction mixture is maintained at a temperature of 56° C. for 45 seconds (annealing phase), and at a temperature of 72° C. for one minute (elongation phase). The subsequent denaturation steps (at 94° C.) last for 45 seconds. After 30 reaction cycles, a concluding elongation step (at 72° C.), of 5-minute duration, is carried out.

The PCR products are separated on a polyacrylamide gel (4%) in a running buffer of Tris-borate (in each case 50 mM) containing EDTA (2.5 mM). In addition, a nucleic acid mixture (for example the product resulting from cleavage of Spp1 phage DNA by the restriction endonuclease EcoRI) is included as a molecular weight standard. Subsequently, the separated PCR products are stained by staining with ethidium bromide (0.1 mg/nml in water), and visualized by irradiation with UV light (260 nm).

The presence of DNA or cells of bacteria from the species *L. monocytogenes*, from the species *L. innocua*, from the group *L. ivanovii/L. seeligeri/L. welshimeri* or from the group *L. grayi/L. murrayi* can be differentiated on the basis of the different molecular weights (see column H in Table 1, as well as FIG. 1).

Example 9

Synthesis of the peptide CysGlnGlnGlnThrAlaProLysAlaProThrGlu(SEQ ID NO:42)

The f$_{moc}$ process (9-fluorenylmethyloxycarbonyl protective group) is used for the synthesis of the peptide CysGlnGlnGInTirAlaProLysAlaProThrGlu(SEQ ID NO:42). This peptide corresponds to a peptide of the formula IVd with an additional N-terminal cysteine residue as linker. A peptide synthesizer from Applied Biosystems is used for the synthesis; the process parameters are contained in the instrument documentation.

A polymeric support with 4-(2'4'-dimethoxyphenylaminomethyl)phenoxy groups serves as the solid phase. The amino acids are employed as α-N-f$_{moc}$ derivatives. Any reactive side groups contained in the amino acids are masked by additional protective groups which may be eliminated by hydrolysis with trifluoroacetic acid. The peptide bonds are produced by activating the carboxyl groups with diisopropylcarbodiimide. The order in which the amino acid derivatives are put in is determined by the desired sequence.

In the first step of the synthesis cycle, the amino group on the solid phase, i.e., in the first cycle the amino groups of the 4-(2'4'-dimethoxyphenylaminomethyl)phenoxy residue of the support, reacts with the carboxyl group of the incoming amino acid, which is employed as the α-N-f$_{moc}$ derivative, where appropriate with protected side chains, and which is activated by diisopropylcarbodiimide, as does the α-amino group of the last amino acid to be attached in the following cycles. Amino acid derivatives which have not reacted are washed out with dimethylformamide. Subsequently, the f$_{moc}$ group is eliminated by treating with 20% (V/V) piperidine in dimethylformamide. The rest of the protective groups remain unaltered during this reaction. Following the removal of the α-N-protective group, the next reaction cycle can begin. Once the last amino acid corresponding to the envisaged sequence has been added, the protective groups of the side chains and the bond with the support resin are cleaved by acid hydrolysis with trifluoroacetic acid. The peptide is subsequently purified by high pressure liquid chromatography.

The remaining peptides with the sequences according to the invention are also synthesized in accordance with the procedure described above.

Example 10

Conjugation of the peptide CysGlnGlnGlnThrAlaProLysAlaProThrGlu(SEQ ID NO:42) with glucose dehydrogenase a) Derivatization of the glucose dehydrogenase: 30 mg of glucose dehydrogenase from *Bacillus megaterium* from Merck (Art. No. 13732) are dissolved in 4 ml of sodium phosphate buffer (50 mM; pH 8.0). 6.78 mg of N-y-maleimidobutyryloxysuccinimide (from Calbiochem), dissolved in 50 µl of dimethyl sulfoxide, are added to 2.4 ml of this solution, and the mixture is left to stand at room temperature for 30 minutes. Subsequently, the excess N-y-maleimidobutyryloxysuccinimide is separated off chromatographically by gel filtration on PD-10 (from Pharmacia). Following the chromatography, 3.5 ml of a solution of the activated carrier protein are obtained, having a concentration of 4.5 mg/ml.

b) Coupling with the peptide: 5.2 mg of the peptide, prepared according to Example 9 and dissolved in 1 ml of sodium phosphate buffer (50 mM; pH 7.0), are added to 1.1 ml of the solution from the above step and the mixture is left to stand at room temperature for 3 hours. Subsequently, the peptide which has not been bound is separated off chromatographically by gel filtration on PD-10 (from Pharmacia). Following the chromatography, 3.5 ml of a solution of the conjugate are obtained, having a concentration of 2.3 mg/ml.

Conjugates with other peptides corresponding to the present invention are also prepared in accordance with the procedure described above.

Example 11

Production of polyclonal antibodies against the peptide CysGlnGlnGlnThrAlaProLysAlaProThrGlu(SEQ ID NO:42)

Two rabbits are in each case injected intramuscularly with an emulsion consisting of 0.18 ml of conjugate from Example 10, 0.07 ml of phosphate-buffered saline and 0.25 ml of an oil adjuvant (MISA 50, from Seppic, France). Booster injections of the same quantities are given three, five and seven weeks after the initial injection. One week after the last injection, the animals are killed and exsanguinated. After the blood has coagulated, the antiserum is obtained by centrifuigation and sodium azide is added to give a final concentration of 0.02%. The antiserum is stored frozen at −20° C.

Example 12

Production of monoclonal antibodies against the peptide CysGlnGlnGlnThrAlaProLysAlaProThrGlu(SEQ ID NO:42)

Two mice are in each case injected subcutaneously with an emulsion consisting of 0.1 ml of conjugate from Example 10 and 0.1 ml oil adjuvant (MISA 50, from Seppic, France). Booster injections of the same amounts are given two, four and six weeks after the initial injection. Three days after the last injection, the animals are killed and the spleen is isolated. The cells from the spleen are isolated by customary processes and fused with a permanent murine cell line. Cell lines which form antibodies against the peptide CysGlnGlnGlnThrAlaProLysAlaProThrGlu(SEQ ID NO:42) are selected from the fusion products.

Example 13

Immunological detection of *L. monocytogenes* a) Pre-culture and centrifugation of the bacteria: 10 ml of CASO broth are inoculated with material from several colonies of *L. monocytogenes* and incubated at 30° C. overnight. Subsequently, 1 ml of the culture is withdrawn in each case. The bacterial cells are removed by centrifugation (13000 rpm).

b) Identification reaction: In each case 300 μl of the supernatants from the previous step are pipetted into the wells of a microtiter plate and incubated at 4° C. overnight. Subsequently, each well is washed three times with 100 μl of washing solution (9 g/l NaCl and 0.05% Tween 20 in water) on each occasion. 100 μl of antiserum prepared according to Example 11 are now pipetted into each well and the plate is incubated at room temperature for one hour. Each well is once again washed three times with 100 μl of washing solution on each occasion. 100 μl of anti-rabbit antibody solution labelled with alkaline phosphatase (Art. No. A 8025, from Sigma) are then pipefitted into each of the wells, and the plate is incubated at room temperature for 30 minutes. Each of the wells is washed once again with 100 μl of washing solution and the bound, enzyme-labelled antibody is subsequently detected. To do this, 200 μl of a buffer solution containing substrate is added to each well, and the plate is incubated at room temperature for 30 minutes. The reaction is stopped by the addition of 100 μl of 2N NaOH solution (Art. No. 9136, from Merck) to each well, and the reaction product is rendered visible. A yellow-orange coloration indicates the presence of *L. monocytogenes.*

Example 14

Specific detection of *L. monocytogenes* using immunoblotting

Bacteria are pre-cultured as described in Example 13a), and the cells are centrifuged off. The cells which have been centrifuged off are taken up and suspended in 1 ml of phosphate-buffered saline. 2 μl of this suspension are pipetted on to a nitrocellulose membrane (Hybond C, 0.45 μm, Art. No. RPN 283 C, from Amersham). Once the solution has dried in, the membrane is treated at room temperature for one hour with a solution of bovine serum albumin (10 g/l) in phosphate-buffered saline. A dilution (1:200) of the antiserum obtained in Example 11 is prepared using a solution of bovine serum albumin (10 g/l) and Tween 20 (0.5 g/l) in phosphate-buffered saline (antibody solution A), as is a further dilution (1:500) of peroxidase-labelled anti-rabbit antibody (anti-rabbit IgG, Art. No. 68–397; from ICN Immunobiologicals) using the same diluent (HRP-antibody solution). The membrane is incubated at room temperature for one hour with antibody solution A, and subsequently washed three times with phosphate-buffered saline containing 0.05% Tween 20. In order to detect the antibody binding, the membrane is subsequently incubated at room temperature for one hour with HRP-antibody solution and in each case washed three times with a) Tween 20 (0.5 g/l) in phosphate-buffered saline, b) phosphate-buffered saline and c) Tris buffer (50 mM; pH 7.4; containing 200 mM NaCl). For die color reaction, a solution of 4-chloro-1-naphthiol (3 mg/ml in methanol) is diluted with five volumes of Tris buffer (50 mM; pH 7.4; containing 200 mM NaCl), and hydrogen peroxide is added (final concentration 0.1 g/l). The membrane is incubated in this substrate solution. A blue-black coloration indicates *L. monocytogenes.*

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An isolated DNA molecule consisting of a nucleotide sequence selected from one of the formulae (Va)–(Vh), wherein $X^1$ and $X^2$ are each, independently, hydrogen or 1–20 additional nucleotides, $X^1$AATATGAAAAAAGC$X^2$(SEQ ID NO:1) (Va),
$X^1$GCTTCGGTCGCGTA$X^2$(SEQ ID NO:2) (Vb),
$X^1$ACAGCTGGGATTGC$X^2$(SEQ ID NO:3) (Vc),
$X^1$ACTCGTAACACAGCT$X^2$(SEQ ID NO:4) (Vd),
$X^1$TAACAGCAATTCAAG$X^2$(SEQ ID NO:5)(Ve),
$X^1$CTGAGGTAGCGAGC$X^2$(SEQ ID NO:6) (Vf),
$X^1$AGCACTCCAGTTGTTA$X^2$(SEQ ID NO:7) (Vg), or
$X^1$GCAGTTTCTAAACCT$X^2$(SEQ ID NO:8 (Vh), or a DNA segment fully complementary to said DNA molecule consisting of the sequence of formulae (Va)–(Vh), wherein said DNA molecule is useful as a primer for amplifying an iap (invasion-associated protein) gene.

2. An isolated DNA molecule of claim 1, selected from

ATGAATATGAAAAAAGCAAC(SEQ ID NO:9) (IIa),
TTGGCTTCGGTCGCGTATAA(SEQ ID NO:10) (IIb),
GCTACAGCTGGGATTGCGGT(SEQ ID NO:11) (IIc),
CAAACTGCTAACACAGCTACT(SEQ ID NO:12) (IId),
CAATAACAGCAATTCAAGTGC(SEQ ID NO:13) (IIe),
TAACTGAGGTAGCGAGCGAA(SEQ ID NO:14) (IIf),
ACTAGCACTCCAGTTGTTAAAC(SEQ ID NO:15) (IIg), or
CCAGCAGTTTCTAAACCTGCT(SEQ ID NO:16) (IIh), or a DNA segment fully complementary to said DNA molecule consisting of the sequence of formulae (IIa) –(IIh).

3. A method of detecting the presence of a bacteria of the genus Listeria in a sample, comprising hybridizing DNA from the sample with a DNA molecule of claim 1.

4. A method of detecting the presence of a bacteria of the genus Listeria in a sample by means of gene amplification, wherein a primer of claim 1 is used.

5. A test kit for detecting bacteria of the genus Listeria by means of a polymerase chain reaction assay comprising, as a DNA primer, a DNA molecule of claim 1.

6. A test kit of claim 5 for detecting bacteria of the species *Listeria monocytogenes*.

* * * * *

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Listeria monocytogenes
        (B) STRAIN: Mackaness (ix) FEATURE:
        (A) NAME/KEY: misc_feature
        (B) LOCATION: 1-20
        (D) OTHER INFORMATION: /note= "SOME OR ALL N NUCLEOTIDES MAY
            BE ABSENT"

(ix) FEATURE:
        (A) NAME/KEY: misc_feature
        (B) LOCATION: 35-54
        (D) OTHER INFORMATION: /note= "SOME OR ALL N NUCLEOTIDES MAY
            BE ABSENT"

(xi) SEQUENCE DESCRIPTION: SEQ ID NO:1:

NNNNNNNNNN NNNNNNNNNN AATATGAAAA AAGCNNNNNN NNNNNNNNNN NNNN                54

(2) INFORMATION FOR SEQ ID NO:2:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Listeria monocytogenes
        (B) STRAIN: Mackaness (ix) FEATURE:
        (A) NAME/KEY: misc_feature
        (B) LOCATION: 1-20
        (D) OTHER INFORMATION: /note= "SOME OR ALL N NUCLEOTIDES MAY
            BE ABSENT"

(ix) FEATURE:
        (A) NAME/KEY: misc_feature
        (B) LOCATION: 35-54
        (D) OTHER INFORMATION: /note= "SOME OR ALL N NUCLEOTIDES MAY
            BE ABSENT"

(xi) SEQUENCE DESCRIPTION: SEQ ID NO:2:

NNNNNNNNNN NNNNNNNNNN GCTTCGGTCG CGTANNNNNN NNNNNNNNNN NNNN                54

(2) INFORMATION FOR SEQ ID NO:3:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Listeria monocytogenes
             (B) STRAIN: Mackaness (ix) FEATURE:
             (A) NAME/KEY: misc_feature
             (B) LOCATION: 1-20
             (D) OTHER INFORMATION: /note= "SOME OR ALL N NUCLEOTIDES MAY
                 BE ABSENT"

(ix) FEATURE:
             (A) NAME/KEY: misc_feature
             (B) LOCATION: 35-54
             (D) OTHER INFORMATION: /note= "SOME OR ALL N NUCLEOTIDES MAY
                 BE ABSENT"

(xi) SEQUENCE DESCRIPTION: SEQ ID NO:3:

NNNNNNNNNN NNNNNNNNNN ACAGCTGGGA TTGCNNNNNN NNNNNNNNNN NNNN          54

(2) INFORMATION FOR SEQ ID NO:4:

(i) SEQUENCE CHARACTERISTICS:
             (A) LENGTH: 55 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Listeria monocytogenes
             (B) STRAIN: Mackaness (ix) FEATURE:
             (A) NAME/KEY: misc_feature
             (B) LOCATION: 1-20
             (D) OTHER INFORMATION: /note= "SOME OR ALL N NUCLEOTIDES MAY
                 BE ABSENT"

(ix) FEATURE:
             (A) NAME/KEY: misc_feature
             (B) LOCATION: 36-55
             (D) OTHER INFORMATION: /note= "SOME OR ALL N NUCLEOTIDES MAY
                 BE ABSENT"

(xi) SEQUENCE DESCRIPTION: SEQ ID NO:4:

NNNNNNNNNN NNNNNNNNNN ACTGCTAACA CAGCTNNNNN NNNNNNNNNN NNNNN         55

(2) INFORMATION FOR SEQ ID NO:5:

(i) SEQUENCE CHARACTERISTICS:
             (A) LENGTH: 55 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Listeria monocytogenes
             (B) STRAIN: Mackaness (ix) FEATURE:
             (A) NAME/KEY: misc_feature
             (B) LOCATION: 1-20

```
            (D) OTHER INFORMATION: /note= "SOME OR ALL N NUCLEOTIDES MAY
                BE ABSENT"

(ix) FEATURE:
            (A) NAME/KEY: misc_feature
            (B) LOCATION: 36-55
            (D) OTHER INFORMATION: /note= "SOME OR ALL N NUCLEOTIDES MAY
                BE ABSENT"

(xi) SEQUENCE DESCRIPTION: SEQ ID NO:5:

NNNNNNNNNN NNNNNNNNNN TAACAGCAAT TCAAGNNNNN NNNNNNNNNN NNNN        55

(2) INFORMATION FOR SEQ ID NO:6:

(i) SEQUENCE CHARACTERISTICS:
            (A) LENGTH: 54 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Listeria monocytogenes
            (B) STRAIN: Mackaness (ix) FEATURE:
            (A) NAME/KEY: misc_feature
            (B) LOCATION: 1-20
            (D) OTHER INFORMATION: /note= "SOME OR ALL N NUCLEOTIDES MAY
                BE ABSENT"

(ix) FEATURE:
            (A) NAME/KEY: misc_feature
            (B) LOCATION: 35-54
            (D) OTHER INFORMATION: /note= "SOME OR ALL N NUCLEOTIDES MAY
                BE ABSENT"

(xi) SEQUENCE DESCRIPTION: SEQ ID NO:6:

NNNNNNNNNN NNNNNNNNNN CTGAGGTAGC GAGCNNNNNN NNNNNNNNNN NNNN        54

(2) INFORMATION FOR SEQ ID NO:7:

(i) SEQUENCE CHARACTERISTICS:
            (A) LENGTH: 56 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Listeria monocytogenes
            (B) STRAIN: Mackaness (ix) FEATURE:
            (A) NAME/KEY: misc_feature
            (B) LOCATION: 1-20
            (D) OTHER INFORMATION: /note= "SOME OR ALL N NUCLEOTIDES MAY
                BE ABSENT"

(ix) FEATURE:
            (A) NAME/KEY: misc_feature
            (B) LOCATION: 37-56
            (D) OTHER INFORMATION: /note= "SOME OR ALL N NUCLEOTIDES MAY
                BE ABSENT"

(xi) SEQUENCE DESCRIPTION: SEQ ID NO:7:
```

NNNNNNNNNN NNNNNNNNNN AGCACTCCAG TTGTTANNNN NNNNNNNNNN NNNNN        56

(2) INFORMATION FOR SEQ ID NO:8:

(i) SEQUENCE CHARACTERISTICS:
        (A) LENGTH: 55 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Listeria monocytogenes
        (B) STRAIN: Mackaness (ix) FEATURE:
        (A) NAME/KEY: misc_feature
        (B) LOCATION: 1-20
        (D) OTHER INFORMATION: /note= "SOME OR ALL N NUCLEOTIDES MAY
            BE ABSENT"

(ix) FEATURE:
        (A) NAME/KEY: misc_feature
        (B) LOCATION: 36-55
        (D) OTHER INFORMATION: /note= "SOME OR ALL N NUCLEOTIDES MAY
            BE ABSENT"

(xi) SEQUENCE DESCRIPTION: SEQ ID NO:8:

NNNNNNNNNN NNNNNNNNNN GCAGTTTCTA AACCTNNNNN NNNNNNNNNN NNNNN         55

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Listeria monocytogenes
        (B) STRAIN: Mackaness (xi) SEQUENCE DESCRIPTION: SEQ ID NO:9:

ATGAATATGA AAAAAGCAAC                                                20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Listeria monocytogenes
        (B) STRAIN: Mackaness (xi) SEQUENCE DESCRIPTION: SEQ ID NO:10:

TTGGCTTCGG TCGCGTATAA                                                    20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Listeria monocytogenes
        (B) STRAIN: Mackaness (xi) SEQUENCE DESCRIPTION: SEQ ID NO:11:

GCTACAGCTG GGATTGCGGT                                                    20

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Listeria monocytogenes
        (B) STRAIN: Mackaness (xi) SEQUENCE DESCRIPTION: SEQ ID NO:12:

CAAACTGCTA ACACAGCTAC T                                                  21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Listeria monocytogenes
        (B) STRAIN: Mackaness (xi) SEQUENCE DESCRIPTION: SEQ ID NO:13:

CAATAACAGC AATTCAAGTG C                                                  21

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: double (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Listeria monocytogenes
            (B) STRAIN: Mackaness (xi) SEQUENCE DESCRIPTION: SEQ ID NO:14:

TAACTGAGGT AGCGAGCGAA                                                    20

(2) INFORMATION FOR SEQ ID NO:15:

(i) SEQUENCE CHARACTERISTICS:
            (A) LENGTH: 22 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Listeria monocytogenes
            (B) STRAIN: Mackaness (xi) SEQUENCE DESCRIPTION: SEQ ID NO:15:

ACTAGCACTC CAGTTGTTAA AC                                                 22

(2) INFORMATION FOR SEQ ID NO:16:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Listeria monocytogenes
            (B) STRAIN: Mackaness (xi) SEQUENCE DESCRIPTION: SEQ ID NO:16:

CCAGCAGTTT CTAAACCTGC T                                                  21

(2) INFORMATION FOR SEQ ID NO:17:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (vi) ORIGINAL SOURCE:
            (A) ORGANISM: Listeria monocytogenes
            (B) STRAIN: EGD (ix) FEATURE:
            (A) NAME/KEY: Modified-site
            (B) LOCATION: 1-7
            (D) OTHER INFORMATION: /note= "SOME OR ALL Xaa AMINO ACIDS

MAY BE ABSENT"

(ix) FEATURE:
    (A) NAME/KEY: Modified-site
    (B) LOCATION: 14-20
    (D) OTHER INFORMATION: /note= "SOME OR ALL Xaa AMINO ACIDS
        MAY BE ABSENT"

(xi) SEQUENCE DESCRIPTION: SEQ ID NO:17:

Xaa Xaa Xaa Xaa Xaa Xaa Xaa Pro Val Ala Pro Thr Gln Xaa Xaa Xaa
1               5                   10                  15

Xaa Xaa Xaa Xaa
        20

(2) INFORMATION FOR SEQ ID NO:18:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (vi) ORIGINAL SOURCE:
        (A) ORGANISM: Listeria monocytogenes
        (B) STRAIN: EGD (ix) FEATURE:
        (A) NAME/KEY: Modified-site
        (B) LOCATION: 1-7
        (D) OTHER INFORMATION: /note= "SOME OR ALL Xaa AMINO ACIDS
            MAY BE ABSENT"

(ix) FEATURE:
        (A) NAME/KEY: Modified-site
        (B) LOCATION: 15-21
        (D) OTHER INFORMATION: /note= "SOME OR ALL Xaa AMINO ACIDS
            MAY BE ABSENT"

(xi) SEQUENCE DESCRIPTION: SEQ ID NO:18:

Xaa Xaa Xaa Xaa Xaa Xaa Xaa Thr Gln Ala Thr Pro Ala Xaa Xaa
1               5                   10                  15

Xaa Xaa Xaa Xaa Xaa
        20

(2) INFORMATION FOR SEQ ID NO:19:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (vi) ORIGINAL SOURCE:
        (A) ORGANISM: Listeria monocytogenes
        (B) STRAIN: EGD (ix) FEATURE:
        (A) NAME/KEY: Modified-site
        (B) LOCATION: 1-7
        (D) OTHER INFORMATION: /note= "SOME OR ALL Xaa AMINO ACIDS
            MAY BE ABSENT"

(ix) FEATURE:
        (A) NAME/KEY: Modified-site
        (B) LOCATION: 17-23
        (D) OTHER INFORMATION: /note= "SOME OR ALL Xaa AMINO ACIDS
            MAY BE ABSENT"

(xi) SEQUENCE DESCRIPTION: SEQ ID NO:19:

Xaa Xaa Xaa Xaa Xaa Xaa Xaa Ala Ile Lys Gln Thr Ala Asn Thr Ala
1               5                   10                  15

```
        Xaa Xaa Xaa Xaa Xaa Xaa Xaa
                    20

(2) INFORMATION FOR SEQ ID NO:20:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (vi) ORIGINAL SOURCE:
        (A) ORGANISM: Listeria monocytogenes
        (B) STRAIN: EGD (ix) FEATURE:
        (A) NAME/KEY: Modified-site
        (B) LOCATION: 1-7
        (D) OTHER INFORMATION: /note= "SOME OR ALL Xaa AMINO ACIDS
            MAY BE ABSENT"

(ix) FEATURE:
        (A) NAME/KEY: Modified-site
        (B) LOCATION: 17-23
        (D) OTHER INFORMATION: /note= "SOME OR ALL Xaa AMINO ACIDS
            MAY BE ABSENT"

(xi) SEQUENCE DESCRIPTION: SEQ ID NO:20:

Xaa Xaa Xaa Xaa Xaa Xaa Xaa Gln Gln Thr Ala Pro Lys Ala Pro Thr
   1               5                   10                  15

Xaa Xaa Xaa Xaa Xaa Xaa Xaa
                 20

(2) INFORMATION FOR SEQ ID NO:21:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (vi) ORIGINAL SOURCE:
        (A) ORGANISM: Listeria monocytogenes
        (B) STRAIN: EGD (ix) FEATURE:
        (A) NAME/KEY: Modified-site
        (B) LOCATION: 1-7
        (D) OTHER INFORMATION: /note= "SOME OR ALL Xaa AMINO ACIDS
            MAY BE ABSENT"

(ix) FEATURE:
        (A) NAME/KEY: Modified-site
        (B) LOCATION: 20-26
        (D) OTHER INFORMATION: /note= "SOME OR ALL Xaa AMINO ACIDS
            MAY BE ABSENT"

(xi) SEQUENCE DESCRIPTION: SEQ ID NO:21:

Xaa Xaa Xaa Xaa Xaa Xaa Xaa Val Asn Asn Glu Val Ala Ala Ala Glu
   1               5                   10                  15

Lys Thr Glu Xaa Xaa Xaa Xaa Xaa Xaa Xaa
                 20                  25

(2) INFORMATION FOR SEQ ID NO:22:

(i) SEQUENCE CHARACTERISTICS:
        (A) LENGTH: 23 amino acids
        (B) TYPE: amino acid
        (D) TOPOLOGY: linear
```

```
    (ii) MOLECULE TYPE: peptide (vi) ORIGINAL SOURCE:
         (A) ORGANISM: Listeria monocytogenes
         (B) STRAIN: EGD (ix) FEATURE:
         (A) NAME/KEY: Modified-site
         (B) LOCATION: 1-7
         (D) OTHER INFORMATION: /note= "SOME OR ALL Xaa AMINO ACIDS
             MAY BE ABSENT"

(ix) FEATURE:
         (A) NAME/KEY: Modified-site
         (B) LOCATION: 17-23
         (D) OTHER INFORMATION: /note= "SOME OR ALL Xaa AMINO ACIDS
             MAY BE ABSENT"

(xi) SEQUENCE DESCRIPTION: SEQ ID NO:22:

Xaa Xaa Xaa Xaa Xaa Xaa Xaa Thr Pro Val Val Lys Gln Glu Val Lys
    1               5                  10                  15

Xaa Xaa Xaa Xaa Xaa Xaa Xaa
                 20

(2) INFORMATION FOR SEQ ID NO:23:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (vi) ORIGINAL SOURCE:
         (A) ORGANISM: Listeria monocytogenes
         (B) STRAIN: EGD (ix) FEATURE:
         (A) NAME/KEY: Modified-site
         (B) LOCATION: 1-7
         (D) OTHER INFORMATION: /note= "SOME OR ALL Xaa AMINO ACIDS
             MAY BE ABSENT"

(ix) FEATURE:
         (A) NAME/KEY: Modified-site
         (B) LOCATION: 19-25
         (D) OTHER INFORMATION: /note= "SOME OR ALL Xaa AMINO ACIDS
             MAY BE ABSENT"

(xi) SEQUENCE DESCRIPTION: SEQ ID NO:23:

Xaa Xaa Xaa Xaa Xaa Xaa Xaa Val Lys Gln Pro Thr Thr Gln Gln Thr
    1               5                  10                  15

Ala Pro Xaa Xaa Xaa Xaa Xaa Xaa Xaa
                 20                  25

(2) INFORMATION FOR SEQ ID NO:24:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (vi) ORIGINAL SOURCE:
         (A) ORGANISM: Listeria monocytogenes
         (B) STRAIN: EGD (ix) FEATURE:
         (A) NAME/KEY: Modified-site
         (B) LOCATION: 1-7
         (D) OTHER INFORMATION: /note= "SOME OR ALL Xaa AMINO ACIDS
             MAY BE ABSENT"
```

-continued

```
    (ix) FEATURE:
         (A) NAME/KEY: Modified-site
         (B) LOCATION: 18-24
         (D) OTHER INFORMATION: /note= "SOME OR ALL Xaa AMINO ACIDS
             MAY BE ABSENT"

(xi) SEQUENCE DESCRIPTION: SEQ ID NO:24:

Xaa Xaa Xaa Xaa Xaa Xaa Xaa Ile Lys Gln Pro Thr Lys Thr Val Ala
1               5                   10                  15

Pro Xaa Xaa Xaa Xaa Xaa Xaa Xaa
            20

(2) INFORMATION FOR SEQ ID NO:25:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (vi) ORIGINAL SOURCE:
         (A) ORGANISM: Listeria monocytogenes
         (B) STRAIN: EGD (xi) SEQUENCE DESCRIPTION: SEQ ID NO:25:

Gln Gln Thr Thr Thr Lys Ala Pro Thr
1               5

(2) INFORMATION FOR SEQ ID NO:26:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (vi) ORIGINAL SOURCE:
         (A) ORGANISM: Listeria monocytogenes
         (B) STRAIN: EGD (xi) SEQUENCE DESCRIPTION: SEQ ID NO:26:

Val Ser Thr Pro Val Ala Pro Thr Gln
1               5

(2) INFORMATION FOR SEQ ID NO:27:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (vi) ORIGINAL SOURCE:
         (A) ORGANISM: Listeria monocytogenes
         (B) STRAIN: EGD (xi) SEQUENCE DESCRIPTION: SEQ ID NO:27:

Thr Thr Gln Ala Thr Thr Pro Ala Pro Lys Val Ala
1               5                   10

(2) INFORMATION FOR SEQ ID NO:28:

(i) SEQUENCE CHARACTERISTICS:
        (A) LENGTH: 11 amino acids
        (B) TYPE: amino acid
        (D) TOPOLOGY: linear (ii) MOLECULE TYPE: peptide
```

-continued

```
    (vi) ORIGINAL SOURCE:
         (A) ORGANISM: Listeria monocytogenes
         (B) STRAIN: EGD (xi) SEQUENCE DESCRIPTION: SEQ ID NO:28:

Leu Ala Ile Lys Gln Thr Ala Asn Thr Ala Thr
1               5                   10
```

(2) INFORMATION FOR SEQ ID NO:29:

```
    (i) SEQUENCE CHARACTERISTICS:
        (A) LENGTH: 11 amino acids
        (B) TYPE: amino acid
        (D) TOPOLOGY: linear (ii) MOLECULE TYPE: peptide (vi) ORIGINAL SOURCE:
        (A) ORGANISM: Listeria monocytogenes
        (B) STRAIN: EGD (xi) SEQUENCE DESCRIPTION: SEQ ID NO:29:

Gln Gln Gln Thr Ala Pro Lys Ala Pro Thr Glu
1               5                   10
```

(2) INFORMATION FOR SEQ ID NO:30:

```
    (i) SEQUENCE CHARACTERISTICS:
        (A) LENGTH: 12 amino acids
        (B) TYPE: amino acid
        (D) TOPOLOGY: linear (ii) MOLECULE TYPE: peptide (vi) ORIGINAL SOURCE:
        (A) ORGANISM: Listeria monocytogenes
        (B) STRAIN: EGD (xi) SEQUENCE DESCRIPTION: SEQ ID NO:30:

Ser Thr Pro Val Ala Pro Thr Gln Glu Val Lys Lys
1               5                   10
```

(2) INFORMATION FOR SEQ ID NO:31:

```
    (i) SEQUENCE CHARACTERISTICS:
        (A) LENGTH: 10 amino acids
        (B) TYPE: amino acid
        (D) TOPOLOGY: linear (ii) MOLECULE TYPE: peptide (vi) ORIGINAL SOURCE:
        (A) ORGANISM: Listeria monocytogenes
        (B) STRAIN: EGD (xi) SEQUENCE DESCRIPTION: SEQ ID NO:31:

Pro Val Ala Pro Thr Gln Glu Val Lys Lys
1               5                   10
```

(2) INFORMATION FOR SEQ ID NO:32:

```
    (i) SEQUENCE CHARACTERISTICS:
        (A) LENGTH: 14 amino acids
        (B) TYPE: amino acid
        (D) TOPOLOGY: linear (ii) MOLECULE TYPE: peptide (vi) ORIGINAL SOURCE:
        (A) ORGANISM: Listeria monocytogenes
        (B) STRAIN: EGD
```

(xi) SEQUENCE DESCRIPTION: SEQ ID NO:32:

Gln Val Asn Asn Glu Val Ala Ala Ala Glu Lys Thr Glu Lys
1               5                   10

(2) INFORMATION FOR SEQ ID NO:33:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (vi) ORIGINAL SOURCE:
        (A) ORGANISM: Listeria monocytogenes
        (B) STRAIN: EGD (xi) SEQUENCE DESCRIPTION: SEQ ID NO:33:

Glu Val Lys Gln Thr Thr Gln Ala Thr Thr Pro Ala
1               5                   10

(2) INFORMATION FOR SEQ ID NO:34:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (vi) ORIGINAL SOURCE:
        (A) ORGANISM: Listeria monocytogenes
        (B) STRAIN: EGD (xi) SEQUENCE DESCRIPTION: SEQ ID NO:34:

Ala Ile Lys Gln Thr Ala Asn Thr Ala Thr Pro Lys
1               5                   10

(2) INFORMATION FOR SEQ ID NO:35:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (vi) ORIGINAL SOURCE:
        (A) ORGANISM: Listeria innocua (xi) SEQUENCE DESCRIPTION: SEQ ID NO:35:

Ser Thr Pro Val Val Lys Gln Glu Val Lys Lys
1               5                   10

(2) INFORMATION FOR SEQ ID NO:36:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (vi) ORIGINAL SOURCE:
        (A) ORGANISM: Listeria innocua (xi) SEQUENCE DESCRIPTION: SEQ ID NO:36:

Glu Val Lys Gln Pro Thr Thr Gln Gln Thr Ala Pro Ala
1               5                   10

(2) INFORMATION FOR SEQ ID NO:37:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (vi) ORIGINAL SOURCE:
        (A) ORGANISM: Listeria innocua (xi) SEQUENCE DESCRIPTION: SEQ ID NO:37:

```
Ala Ile Lys Gln Pro Thr Lys Thr Val Ala Pro Lys
1               5                   10
```

(2) INFORMATION FOR SEQ ID NO:38:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (vi) ORIGINAL SOURCE:
        (A) ORGANISM: Listeria innocua (xi) SEQUENCE DESCRIPTION: SEQ ID NO:38:

```
Glu Gln Gln Thr Thr Thr Lys Ala Pro Thr Gln
1               5                   10
```

(2) INFORMATION FOR SEQ ID NO:39:

(i) SEQUENCE CHARACTERISTICS:
        (A) LENGTH: 232 amino acids
        (B) TYPE: amino acid
        (D) TOPOLOGY: linear (ii) MOLECULE TYPE: peptide (vi) ORIGINAL SOURCE:
        (A) ORGANISM: Listeria monocytogenes
        (B) STRAIN: EGD (xi) SEQUENCE DESCRIPTION: SEQ ID NO:39:

```
Gln Val Asn Asn Glu Val Ala Ala Glu Lys Thr Glu Lys Ser Val
1               5                   10                  15

Ser Ala Thr Trp Leu Asn Val Arg Thr Gly Ala Gly Val Asp Asn Ser
                20                  25                  30

Ile Ile Thr Ser Ile Lys Gly Gly Thr Lys Val Thr Val Glu Thr Thr
                35                  40                  45

Glu Ser Asn Gly Trp His Lys Ile Thr Tyr Asn Asp Gly Lys Thr Gly
            50                  55                  60

Phe Val Asn Gly Lys Tyr Leu Thr Asp Lys Ala Val Ser Thr Pro Val
65                  70                  75                  80

Ala Pro Thr Gln Glu Val Lys Lys Glu Thr Thr Thr Gln Gln Ala Ala
                85                  90                  95

Pro Val Ala Glu Thr Lys Thr Glu Val Lys Gln Thr Thr Gln Ala Thr
                100                 105                 110

Thr Pro Ala Pro Lys Val Ala Glu Thr Lys Glu Thr Pro Val Ile Asp
            115                 120                 125

Gln Asn Ala Thr Thr His Ala Val Lys Ser Gly Asp Thr Ile Trp Ala
            130                 135                 140

Leu Ser Val Lys Tyr Gly Val Ser Val Gln Asp Ile Met Ser Trp Asn
```

```
        145                 150                 155                 160

Asn Leu Ser Ser Ser Ile Tyr Val Gly Gln Lys Leu Ala Ile Lys
                    165                 170                 175

Gln Thr Ala Asn Thr Ala Thr Pro Lys Ala Glu Val Lys Thr Glu Ala
                180                 185                 190

Pro Ala Ala Glu Lys Gln Ala Ala Pro Val Val Lys Glu Asn Thr Asn
                195                 200                 205

Thr Asn Thr Ala Thr Thr Glu Lys Lys Glu Thr Ala Thr Gln Gln Gln
            210                 215                 220

Thr Ala Pro Lys Ala Pro Thr Glu
    225                 230

(2) INFORMATION FOR SEQ ID NO:40:

(i) SEQUENCE CHARACTERISTICS:
        (A) LENGTH: 478 amino acids
        (B) TYPE: amino acid
        (D) TOPOLOGY: linear (ii) MOLECULE TYPE: peptide (vi) ORIGINAL SOURCE:
        (A) ORGANISM: Listeria monocytogenes
        (B) STRAIN: EGD (xi) SEQUENCE DESCRIPTION: SEQ ID NO:40:

Met Asn Met Lys Lys Ala Thr Ile Ala Ala Thr Ala Gly Ile Ala Val
    1               5                   10                  15

Thr Ala Phe Ala Ala Pro Thr Ile Ala Ser Ala Ser Thr Val Val
                20                  25                  30

Glu Ala Gly Asp Thr Leu Trp Gly Ile Ala Gln Ser Lys Gly Thr Thr
                35                  40                  45

Val Asp Ala Ile Lys Lys Ala Asn Asn Leu Thr Thr Asp Lys Ile Val
    50                  55                  60

Pro Gly Gln Lys Leu Gln Val Asn Asn Glu Val Ala Ala Ala Glu Lys
    65                  70                  75                  80

Thr Glu Lys Ser Val Ser Ala Thr Trp Leu Asn Val Arg Thr Gly Ala
                    85                  90                  95

Gly Val Asp Asn Ser Ile Ile Thr Ser Ile Lys Gly Gly Thr Lys Val
                    100                 105                 110

Thr Val Glu Thr Thr Glu Ser Asn Gly Trp His Lys Ile Thr Tyr Asn
                115                 120                 125

Asp Gly Lys Thr Gly Phe Val Asn Gly Lys Tyr Leu Thr Asp Lys Ala
            130                 135                 140

Val Ser Thr Pro Val Ala Pro Thr Gln Glu Val Lys Lys Glu Thr Thr
    145                 150                 155                 160

Thr Gln Gln Ala Ala Pro Val Ala Glu Thr Lys Thr Glu Val Lys Gln
                    165                 170                 175

Thr Thr Gln Ala Thr Thr Pro Ala Pro Lys Val Ala Glu Thr Lys Glu
                180                 185                 190

Thr Pro Val Ile Asp Gln Asn Ala Thr Thr His Ala Val Lys Ser Gly
                195                 200                 205

Asp Thr Ile Trp Ala Leu Ser Val Lys Tyr Gly Val Ser Val Gln Asp
            210                 215                 220

Ile Met Ser Trp Asn Asn Leu Ser Ser Ser Ile Tyr Val Gly Gln
    225                 230                 235                 240

Lys Leu Ala Ile Lys Gln Thr Ala Asn Thr Ala Thr Pro Lys Ala Glu
                    245                 250                 255
```

```
          Val Lys Thr Glu Ala Pro Ala Ala Glu Lys Gln Ala Ala Pro Val Val
                      260                 265                 270

Lys Glu Asn Thr Asn Thr Asn Thr Ala Thr Thr Glu Lys Lys Glu Thr
                      275                 280                 285

Ala Thr Gln Gln Gln Thr Ala Pro Lys Ala Pro Thr Glu Ala Ala Lys
                      290                 295                 300

Pro Ala Pro Ala Pro Ser Thr Asn Thr Asn Ala Asn Lys Thr Asn Thr
          305                 310                 315                 320

Asn Thr Asn Thr Asn Asn Thr Asn Thr Pro Ser Lys Asn Thr Asn Thr
                      325                 330                 335

Asn Ser Asn Thr Asn Thr Asn Thr Asn Ser Asn Thr Asn Ala Asn Gln
                      340                 345                 350

Gly Ser Ser Asn Asn Asn Ser Asn Ser Ser Ala Ser Ala Ile Ile Ala
                      355                 360                 365

Glu Ala Gln Lys His Leu Gly Lys Ala Tyr Ser Trp Gly Gly Asn Gly
                      370                 375                 380

Pro Thr Thr Phe Asp Cys Ser Gly Tyr Thr Lys Tyr Val Phe Ala Lys
          385                 390                 395                 400

Ala Gly Ile Ser Leu Pro Arg Thr Ser Gly Ala Gln Tyr Ala Ser Thr
                      405                 410                 415

Thr Arg Ile Ser Glu Ser Gln Ala Lys Pro Gly Asp Leu Val Phe Phe
                      420                 425                 430

Asp Tyr Gly Ser Gly Ile Ser His Val Gly Ile Tyr Val Gly Asn Gly
                      435                 440                 445

Gln Met Ile Asn Ala Gln Asp Asn Gly Val Lys Tyr Asp Asn Ile His
                      450                 455                 460

Gly Ser Gly Trp Gly Lys Tyr Leu Val Gly Phe Gly Arg Val
          465                 470                 475

(2) INFORMATION FOR SEQ ID NO:41:

(i) SEQUENCE CHARACTERISTICS:
           (A) LENGTH: 12 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:41:

Thr Asn Thr Asn Thr Asn Thr Asn Thr Asn Thr Asn
       1               5                  10

(2) INFORMATION FOR SEQ ID NO:42:

(i) SEQUENCE CHARACTERISTICS:
           (A) LENGTH: 12 amino acids
           (B) TYPE: amino acid
           (D) TOPOLOGY: linear (ii) MOLECULE TYPE: peptide (xi) SEQUENCE DESCRIPTION: SEQ ID NO:42:

Cys Gln Gln Gln Thr Ala Pro Lys Ala Pro Thr Glu
       1               5                  10

(2) INFORMATION FOR SEQ ID NO:43:

(i) SEQUENCE CHARACTERISTICS:
           (A) LENGTH: 21 base pairs
           (B) TYPE: nucleic acid
```

```
       (C) STRANDEDNESS: double
       (D) TOPOLOGY: linear (ii) MOLECULE TYPE: DNA (genomic)

(iii) HYPOTHETICAL: NO (iv) ANTI-SENSE: YES (vi) ORIGINAL SOURCE:
       (A) ORGANISM: Listeria monocytogenes
       (B) STRAIN: Mackaness (xi) SEQUENCE DESCRIPTION: SEQ ID NO:43:

GCACTTGAAT TGCTGTTATT G                                                      21
```